United States Patent [19]

Sunshine et al.

[11] Patent Number: 4,749,711
[45] Date of Patent: Jun. 7, 1988

[54] COUGH/COLD MIXTURES COMPRISING NON-STEROIDAL ANTI-INFLAMMATORY DRUGS

[75] Inventors: Abraham Sunshine, New York; Eugene M. Laska, Larchmont; Carole E. Siegel, Mamaroneck, all of N.Y.

[73] Assignee: Analgesic Associates, Larchmont, N.Y.

[21] Appl. No.: 16,377

[22] Filed: Feb. 19, 1987

Related U.S. Application Data

[62] Division of Ser. No. 887,205, Jul. 21, 1986, which is a division of Ser. No. 752,546, Jul. 8, 1985, Pat. No. 4,619,934, which is a division of Ser. No. 598,502, Apr. 9, 1984, Pat. No. 4,552,899.

[51] Int. Cl.$^4$ .............................................. A61K 31/54
[52] U.S. Cl. ................................................. 514/226.5
[58] Field of Search ......................................... 514/222

[56] References Cited

U.S. PATENT DOCUMENTS 4,322,427  3/1982  Buyniski ............................... 514/288

FOREIGN PATENT DOCUMENTS 0097953  1/1984  European Pat. Off. .

OTHER PUBLICATIONS

Unlisted Drugs, vol. 20, No. 11, Nov. 1968, p. 169n, "Sinubid".
Unlisted Drugs, vol. 23, No. 3, Mar. 1971, p. 36, "Co-Tylenol".
Traber, Daniel L., "Ibuprofen and Diphenhydramine reduce the Lung Lesion of Endotoxemia in Sheep", *J. Trauma*, 1984, 24(9), 835–40.

*Primary Examiner*—Stanley J. Friedman
*Attorney, Agent, or Firm*—Burns, Doane, Swecker & Mathis

[57] ABSTRACT

Pharmaceutical compositions and methods of using same comprising a non-steroidal anti-inflammatory drug in combination with at least one other active component selected from an antihistamine, decongestant, cough suppressant (antitussive) or expectorant are provided for the relief of cough, cold and cold-like symptoms.

17 Claims, No Drawings

COUGH/COLD MIXTURES COMPRISING NON-STEROIDAL ANTI-INFLAMMATORY DRUGS

CROSS-REFERENCE TO RELATED APPLICATIONS

This application is a divisional of application Ser. No. 887,205, filed July 21, 1986; which is a divisional application of Ser. No. 752,546, filed July 8, 1985, now U.S. Pat. No. 4,619,934; which is a divisional application of Ser. No. 598,502, filed Apr. 9, 1984, now U.S. Pat. No. 4,552,899. Other related divisional applications include Ser. No. 016,333, Ser. No. 016,344, Ser. No. 016,377, Ser. No. 016,396, Ser. No. 016,397, Ser. No. 016,398 and Ser. No. 016,563, all of which were filed Feb. 19, 1987.

BACKGROUND OF THE INVENTION

The present invention relates generally to novel pharmaceutical compositions of matter comprising one or more non-steroidal anti-inflammatory drugs (NSAID) in combination with at least one antihistamine, sympathomimetic drug (nasal decongestant, bronchodilator) cough suppressant and/or expectorant, optionally in combination with suitable pharmaceutically acceptable non-toxic carriers or excipients, and to methods of using said compositions in the treatment, management or mitigation of cough, cold, cold-like and/or flu symptoms and the discomfort, pain, fever and general malaise associated therewith.

Non-narcotic analgesics, most of which are also known as non-steroidal anti-inflammatory drugs (NSAID), are widely administered orally in the treatment of mild to severe pain. Within this class, the compounds vary widely in their chemical structure and in their biological profiles as analgesics, anti-inflammatory agents and antipyretic agents. Among the most commonly used members of the non-narcotic analgesic class of drugs are aspirin, acetaminophen and phenacetin. Aspirin and acetaminophen have heretofore been included as the pain reliever and fever-reducing component in conventional cough/cold multi-symptom alleviating compositions.

However, a number of alternative non-narcotic agents offering a variety of advantages over these conventionally employed non-narcotic analgesic antipyretics have now been developed. The principal advantages of these non-steroidal anti-inflammatory drugs include not only the clinically superior analgesic, anti-inflammatory and antipyretic activity of these agents compared to aspirin, acetaminophen or phenacetin, but also a minimization of the adverse side affects experienced with these conventional agents; more specifically, the gastrointestinal ulcerations experienced with aspirin and the hepatic toxicity prevalent with the chronic use of acetaminophen.

Exemplary prior art cough/cold formulations containing aspirin or acetaminophen include Coricidin ®, Coricidin D ®, Comtrex ®, Dristan ®, Daycare ®, Cotylenol ®, Sinubid ® and the like. These formulations generally contain in addition to aspirin or acetaminophen, one or more antihistaminics, decongestants, cough suppressants, antitussives and expectorants.

While aspirin and acetaminophen have been utilized in these previous compositions, it has not been heretofore proposed to use any of the newer non-steroidal anti-inflammatory drugs (i.e., excluding aspirin, acetaminophen and phenacetin) in the preparation of advantageous cough/cold pharmaceutical compositions.

SUMMARY OF THE INVENTION

It is, therefore, a primary object of the present invention to provide pharmaceutical compositions of matter comprising an analgesically effective amount of a non-steroidal anti-inflammatory drug (NSAID) in combination with at least one of an antihistamine, decongestant, cough suppressant, expectorant and, optionally, including pharmaceutically acceptable carriers therefor.

It is a further object of the present invention to provide methods for the symptomatic relief of cough, cold, cold-like and flu symptoms by the administration of preselected dosages of the pharmaceutical compositions of the present invention. Cold-like symptons as used herein refers to coryza, nasal congestion, upper respiratory infections, allergic rhinitis, otitis, sinusitis, etc.

Another object of the present invention is to provide suitable dosage unit forms of one or more NSAID's in combination with at least one of the aforementioned antihistamines, decongestants, etc. adapted for convenient oral administration.

DETAILED DESCRIPTION OF THE INVENTION

More specifically, the applicants herein have found that certain non-steroidal anti-inflammatory agents are ideally suited for use in cough/cold formulations by reason of their enhanced analgesic anti-inflammatory and antipyretic activity and low incidence of untoward side effects, particularly at the optimum dosages provided for in the present invention, compared to aspirin or acetaminophen.

The superiority of various of the non-narcotic analgesics belonging to the non-steroidal anti-inflammatory drug class in comparative studies with aspirin and acetaminophen is well documented in the literature.

Cooper in 1977 found that ibuprofen 400 mg had a greater peak effect and longer duration of action than aspirin 650 mg. Cooper, S. A., Needle, A. E., Kruger, G. O. 1977. "An Analgesic Relative Potency Assay Comparing Aspirin, Ibuprofen and Placebo." *Oral Surg.* 35: 898–903. Cooper in another study in 1982 found 400 mg of ibuprofen to be more effective than aspirin 650 mg. Cooper, S. A., Engel, J., Ladov, M., Precheur, H., Rosenheck, A., Rauch, D. 1982. "Analgesic Efficacy of an Ibuprofen-codeine Combination." *Pharmacotherapy* 2: 162–67. Sunshine et al found ibuprofen to be significantly superior to aspirin in the relief of post-episiotomy pain. Sunshine, A. et al, *Clinical Pharmacology and Therapeutics*: 24: 254–250, 1983.

Dionne in 1982 found ibuprofen to be more effective than acetaminophen in delaying the onset and intensity of post-operative dental pain. Dione, R. A., Campbell, R. A., Cooper, S. A., Hall, D. L., Buckingham, B. "Suppression of Post operative Pain by Preoperative Administration of Ibuprofen in Comparison to Placebo, Acetaminophen and Acetaminophen Plus Codeine." *J. Clin. Phamacol.* (In press).

Naproxen sodium 550 mg was compared with 650 mg of aspirin and was found to provide earlier and better pain relief than aspirin by Sevelius, H., *J. Clin. Pharmacol.* 20: 480–485, 1980. "Comparative Analgesic Effects of Naproxen Sodium, Aspirin and Placebo."

Flurbiprofen 50 and 100 mg was significantly more effective than aspirin 600 mg. Flurbiprofen 25 mg was slightly less effective than aspirin 600 mg. Sunshine, A., Olson N. Z., Laska, E. M. Zighelboim, I., DeCastro, A., Desarrazin, C., *Pharmaco Ther.* 3: 177–181. "Analgesic Effect of Graded Doses of Flurbiprofen in Postepisiotomy Pain".

Silberman found suprofen 200 mg more effective than aspirin 650 mg for pain relief in the treatment of moderate to severe pain resulting from musculoskeletal pain. Silberman, H. M. "Multiple-Dose Comparison of Suprofen, Aspirin and Placebo in the Treatment of Musculoskeletal Pain." *Pharmacology* 27: S 1, 65–73 (1983).

While these reported findings with respect to the outstanding analgesic properties of the non-steroidal anti-inflammatory drugs compared to aspirin or acetetaminophen have prompted the widespread acceptance and usage of these newer non-narcotic analgesics, as single entities, for the treatment and management of acute and chronic inflammatory states, notably rheumatoid arthritis and osteoarthritis, the utilization of these agents in cough/cold compositions has not heretofore been considered.

The non-steroidal anti-inflammatory drugs (NSAID's) for use in the pharmaceutical compositions and methods of use of the present invention may be selected from any of the following categories:

(1) The propionic acid derivatives;
(2) The acetic acid derivatives;
(3) The fenamic acid derivatives;
(4) The biphenylcarboxylic acid derivatives; and
(5) The oxicams.

Accordingly, the term "NSAID" as used herein is intended to mean any non-narcotic analgesic non-steroidal anti-inflammatory compound, including the pharmaceutically acceptable non-toxic salts thereof, falling within one of the five structural categories above but excluding aspirin, acetaminophen and phenacetin.

The specific compounds falling within the foregoing definition of the non-steroidal anti-inflammatory drugs for use in the present invention are well known to those skilled in the art and reference may be had to various literature reference sources for their chemical structures, pharmacological activities, side effects, normal dosage ranges, etc. See, for example, *Physician's Desk Reference*, 35th Edition, 1981 and *The Merck Index*, 9th Edition, Merck and Company, Rahway, N.J. (1976) and *Cutting's Handbook of Pharmacology*, 6th Edition, Ed. T. Z. Czacky, M. D., Appleton-Century-Crofts, New York, 1979, Chapter 49: 538–550.

Of the propionic acid derivatives for use herein, ibuprofen, naproxen, flurbiprofen, fenoprofen, ketoprofen, suprofen, fenbufen, and fluprofen may be mentioned as particularly preferred compounds.

Of the acetic acid derivatives, presently preferred members include tolmetin sodium, zomepirac, sulindac and indomethacin.

Of the fenamic acid derivatives, particularly preferred compounds include mefenamic acid and meclofenamate sodium.

The particularly preferred biphenylcarboxylic acid derivatives for use in the present invention include diflunisal and flufenisal.

The particularly advantageous oxicams include piroxicam, sudoxicam and isoxicam.

Of course, it will be appreciated by those skilled in the art, that any of the foregoing compounds may be utilized in the form of their pharmaceutically acceptable salt forms, e.g., $-COO^-Na^+$, $-COO^-K^+$, and the like.

Of the foregoing non-steroidal anti-inflammatory drugs, in the practice of the preferred embodiments of the present invention, ibuprofen and naproxen are most preferred.

With respect to the dosage amount of the non-steroidal anti-inflammatory drugs in the compositions of the invention, although the specific dose will vary depending upon the age and weight of the patient, the severity of the symptons, the incidence of side effects and the like, for humans, typical effective analgesic amounts of presently preferred NSAID's for use in unit dose compositions of the invention are about 100–500 mg diflunisal, about 25–100 mg zomepirac sodium, about 50–400 mg ibuprofen, most preferably 100–200 mg, about 125–500 mg naproxen, about 25–100 mg flurbiprofen, about 50–100 mg fenoprofen, about 10–20 mg piroxicam, about 125–250 mg mefenamic acid, about 100–400 mg fenbufen or about 25–50 mg ketoprofen; however, greater or lesser amounts may be employed if desired or necessary. With respect to the compounds set forth hereinabove falling within the propionic acid derivative category, suitable dosage ranges for these compounds will generally fall within the range of 25 mg to 600 mg in each unit dose.

A complete description of the various NSAID's, including acceptable analgesically effective amounts thereof for use in unit dose compositions of the present invention also appears in applicants co-pending U.S. Application Ser. Nos. 474,358, filed Mar. 11, 1983, now U.S. Pat. No. 4,486,436, and 578,288, filed Feb. 8, 1984, now U.S. Pat. No. 4,522,826, the entire disclosures of which are incorporated herein by reference.

The cough/cold pharmaceutical compositions of the present invention comprise, in addition to the non-steroidal anti-inflammatory drugs, at least one active ingredient from the following pharmacological classes: antihistamines, sympathomimetics (decongestants), cough suppressants-antitussives and expectorants. Typical therapeutically active components from these categories, along with their usual adult dosage, for use in the pharmaceutical compositions and methods of the invention are set forth in the following Table 1.

Among such Table 1 antihistamines, sympathomimetics, cough suppressants-antitussives and expectorants, in combination with a non-steroidal anti-inflammatory drug, applicants have already demonstrated a synergistically enhanced analgesic and anti-inflammatory response in a mammalian organism. Again compare their copending application, Ser. No. 578,288, filed Feb. 8, 1984, now U.S. Pat. No. 4,522,826.

TABLE I

| DRUG(FORM-SALT) | ACTION[1] | PREPARATIONS | USUAL SINGLE DOSE (ADULT) |
|---|---|---|---|
| chloropheniramine (maleate) | A | Tablets, Capsules, 4 mg, 8 mg, 12 mg, (substained Action) 12 mg | 2–4 mg |
| brompheniramine | A | Tablets, Capsules, | 8–12 mg |

TABLE I-continued

| DRUG(FORM-SALT) | ACTION[1] | PREPARATIONS | USUAL SINGLE DOSE (ADULT) |
|---|---|---|---|
| (maleate) | | 4 mg, 8 mg, 12 mg (Extentabs R) | |
| dexchlorpheniramine (maleate) | A | Tablets, 2 mg, 4 mg, 6 mg, Syrup, Expectorant (2 mg/5 cc) | 2-6 mg |
| dexbrompheniramine (maleate) | A | Tablet, 6 mg | 6 mg |
| triprolidine (HCl) | A | Tablet, 2.5 mg. Syrup - 1.25 mg/5 cc | 1.25-2.5 mg |
| diphenhydramine (HCl) | A | Tablets, Capsules, Elixir, Parenteral, 25 mg, 50 mg 12.5 mg/5 cc; 10-50 mg/ml. | 12.5-50 mg |
| doxylamine (succinate) | A | Tablets, Elixir 10 mg, 7.5 mg/10 cc., | 7.5-10 mg |
| tripelennamine (HCl) | A | Tablet, Elixir, 25 mg, 50 mg, 37.5 mg/5 cc. | 25-50 mg. |
| cyproheptadine (HCl) | A | Tablet, Syrup, 4 mg, 1 mg/5 cc | 4 mg. |
| carbinoxamine (maleate) | A | Syrup 4 mg/5 cc., | 4 mg. |
| bromodiphenhydramine (HCl) | A | Syrup 3.75 mg/5 cc | 3.75 mg. |
| phenindamine (tartrate) | A | Tablet, Elixir 10 mg, 5 mg/5 cc. | 10 mg. |
| pyrilamine (maleate, tannante) | A | Tablet 12.5 mg. | 12.5 mg. |
| azatadine (maleate) | A | Tablet, 1 mg. | 1-2 mg. |
| pseudoephedrine (HCl) | D | Tablet, Capsule 30 mg, 60 mg, 120 mg (sustained action) | 60-120 mg. |
| phenylpropanolamine (HCl) | D | Tablet, Capsule, Elixir, 25 mg, 50 mg, 12.5 mg/5 cc | 25-50 mg. |
| phenylephrine (bitartrate, tannate, HBr, HCl) | D | Tablet, Capsule Elixir, 5 mg, 10 mg, 25 mg, 5 mg/5 cc. | 5-25 mg. |
| caramiphen (edisylate) | CS | Capsule, Elixir 20 mg 5 mg/5 cc | 5-20 mg. |
| dextromethorphan (HBr) | CS | Tablet, Capsule Elixir 15 mg. 30 mg. 15 mg/5 cc. | 30 mg. |
| codeine (phosphate, sulfate) | CS | Tablet, Elixir 10 mg, 10 mg/5 cc. | 10 mg. |
| terpin hydrate | E | Tablet 300 mg. | 300 mg. |
| guaifenesin (glyceryl guaiacolate) | E | Tablet, Capsule Elixir, 100 mg, 100 mg/5 cc. | 100 mg. |
| potassium (Iodide, citrate) | E | Tablet, Elixir, 100 mg, 100 mg/5 cc. | 150-300 mg. |
| potassium guaicolsulfonate | E | Elixir 80 mg/5 cc. | 80 mg |

[1] A = antihistamine
D = decongestant
CS = cough suppressant
E = expectorant

In the pharmaceutical compositions and methods of the present invention, the foregoing active ingredients will be combined with the non-steroidal anti-inflammatory drug(s) and will typically be administered in admixture with suitable pharmaceutical diluents, excipients or carriers (collectively referred to herein as "carrier" materials) suitably selected with respect to the intended form of administration, i.e., oral tablets, capsules, elixirs, syrups, etc. and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, ethyl alcohol (liquid forms) and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, etc. Disintegrators include, without limitation, starch, methylcellulose, agar, bentonite, guar gum, etc. Sweetening and flavoring agents and preservatives can also be included where appropriate.

Of course, additionally, the compositions of the present invention may be formulated in sustained release form to provide the rate controlled release of any one or more of the components to optimize the therapeutic effects, i.e., analgesia, antihistaminic, etc. while minimizing undesirable side effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

As representative suitable formulations consistent with the objects, features and advantages of the present invention, the following non-limiting examples are provided.

EXAMPLE 1

Ibuprofen—200 mg
Chlorpheniramine maleate—8 mg
Phenylpropanolamine hydrochloride—8 mg
Dextromethorphan hydrobromide—30 mg
Guaifenesin—100 mg
  Triturate active ingredients and q.s. with lactose to selected capsule size

EXAMPLE 2

In each fluid ounce:
Naproxen (sodium) 250 mg, dextromethorphan HB 30 mg, phenylpropanolamine hydrochloride 25 mg, orange flavoring and alcohol 10% v/v.

From the foregoing, other typical acceptable pharmaceutical formulations will be apparent to those skilled in the art of pharmaceutical formulations.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove with respect to the active ingredients may be applicable as a consequence of variations of the responsiveness of the mammal treated, severity of symptoms, dosage related adverse effects, if any, observed and similar considerations. Accordingly, such expected variations or differences in the practice of the present invention and the results obtained are contemplated in accordance with the objects and practices of the present invention. It is intended, therefore that the invention be limited only by the scope of the claims which follow.

What is claimed is:

1. A pharmaceutical composition of matter for use in the treatment of cough, cold, cold-like and/or flu symptoms in a mammalian organism, said composition comprising a sympathomimetically, analgesically and anti-inflammatorily effective amount of (i) at least one of the oxicam NSAIDs, piroxicam, sudoxicam, isoxicam, or pharmaceutically acceptable salt thereof, in combinatory immixture with (ii) at least one of the sympathomimetic amines, pseudoephedrine, phenylpropanolamine, phenylephrine, or pharmaceutically acceptable salt thereof.

2. The pharmaceutical composition as defined by claim 1, said NSAID (i) comprising piroxicam or pharmaceutically acceptable salt thereof.

3. The pharmaceutical composition as defined by claim 1, said NSAID (i) comprising sudoxicam or pharmaceutically acceptable salt thereof.

4. The pharmaceutical composition as defined by claim 1, said NSAID (i) comprising isoxicam or pharmaceutically acceptable salt thereof.

5. The pharmaceutically composition as defined by claim 1, comprising at least 10 mg of said NSAID (i).

6. The pharmaceutical composition as defined by claim 5, comprising from 10 mg to 20 mg of said NSAID (i).

7. The pharmaceutical composition as defined by claim 1, comprising (ii) from 60 mg to 120 mg of pseudoephedrine or pharmaceutically acceptable salt thereof.

8. The pharmaceutical composition as defined by claim 1, comprising (ii) from 25 mg to 50 mg of phenylpropanolamine or pharmaceutically acceptable salt thereof.

9. The pharmaceutical composition as defined by claim 1, comprising (ii) from 5 mg to 25 mg of phenylephrine or pharmaceutically acceptable salt thereof.

10. The pharmaceutical composition as defined by claim 1, further comprising (iii) a pharmaceutically acceptable non-toxic carrier.

11. The pharmaceutical composition as defined by claim 1, in oral dosage form.

12. The pharmaceutical composition as defined by claim 11, said oral dosage form comprising a tablet.

13. The pharmaceutical composition as defined by claim 11, said oral dosage form comprising a capsule.

14. The pharmaceutical composition as defined by claim 11, said oral dosage form comprising an elixir.

15. A method for the treatment of cough, cold, cold-like and/or flu symptoms in a mammalian organism in need of such treatment, comprising administering to such organism a symptom relieving, sympathomimetically, analgesically and anti-inflammatorily effective amount of (i) at least one of the oxicam NSAIDs, piroxicam, sudoxicam, isoxicam, or pharmaceutically acceptable salt thereof, in combinatory immixture with (ii) at least one sympathomimetic decongestant or bronchodilator, or pharmaceutically acceptable salt thereof.

16. A method for the treatment of cough, cold, cold-like and/or flu symptoms in a mammalian organism in need of such treatment, comprising administering to such organism the pharmaceutical composition as defined by claim 1.

17. A method for the treatment of cough, cold, cold-like and/or flu symptoms in a mammalian organism in need of such treatment, comprising administering to such organism the pharmaceutical composition as defined by claim 10.

* * * * *